United States Patent [19]

Piccardi et al.

[11] 4,109,011

[45] Aug. 22, 1978

[54] INSECTICIDE CARBAMATES OF N-(POLYCHLOROALLYL)-AMINO-PHENOLS

[75] Inventors: Paolo Piccardi, Milan; Paride Paolucci; Franco Gozzo, both of S. Donato Milanese (Milan); Angelo Longoni, Milan; Vincenzo Dongiovanni, Milan; Giovanni Renis, Milan, all of Italy

[73] Assignee: Montedison S.p.A., Milan, Italy

[21] Appl. No.: 791,332

[22] Filed: Apr. 27, 1977

Related U.S. Application Data

[63] Continuation-in-part of Ser. No. 680,921, Apr. 28, 1976, abandoned.

[30] Foreign Application Priority Data

May 2, 1975 [IT] Italy .................... 22949 A/75

[51] Int. Cl.² .................. A01N 9/12; A01N 9/20; C07C 125/06
[52] U.S. Cl. ................... 424/300; 560/135; 560/136

[58] Field of Search ............ 260/479 C; 424/300; 560/135, 136

[56] References Cited

U.S. PATENT DOCUMENTS 3,819,678   6/1974   Nikles .............................. 260/479 C

OTHER PUBLICATIONS

Journal of Agricultural and Fod Chemistry, Miskus et al., vol. 16, No. 4, pp. 605–607, (1968).

*Primary Examiner*—Jane S. Myers
*Attorney, Agent, or Firm*—Morgan, Finnegan, Pine, Foley & Lee

[57] ABSTRACT

This invention relates to carbamates of N-polychloroallyl-substituted amino-phenols, which are useful as insecticides. More particularly, this invention concerns a new class of carbamates of N-polychloroallyl-substituted amino-phenols, methods for their preparation and methods for their use in combatting moxious insects.

7 Claims, No Drawings

INSECTICIDE CARBAMATES OF N-(POLYCHLOROALLYL)-AMINO-PHENOLS

CROSS-REFERENCE TO RELATED APPLICATIONS

This application is a continuation-in-part of copending application Ser. No. 680,921, filed Apr. 28, 1976, now abandoned.

BACKGROUND OF INVENTION

The aryl N-methyl carbamates represent a well-known class of insecticides which are active towards parasites belonging to different orders and species.

In Nikles, U.S. Pat. No. 3,819,678, there is disclosed a class of carbamates having the general formula:

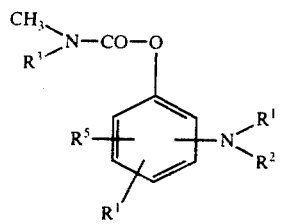

where $R^1$ represents a $C_1$-$C_5$ alkyl, $C_3$-$C_5$ alkenyl or a $C_3$-$C_5$ alkinyl radical or has the same meaning as $R^2$; $R^2$ represents a $C_3$-$C_5$ alkenyl radical substituted by 1 or 2 halogen atoms or a $C_1$-$C_4$ alkyl radical substituted by a $C_1$-$C_4$ alkoxy, $C_1$-$C_4$ alkylmercapto or nitrile group; $R^3$ represents a hydrogen atom or a methyl radical and $R^4$ and $R^5$, the same or different, each represents a hydrogen or a $C_1$-$C_5$ alkyl radical.

These compounds are disclosed as effective pesticides for controlling nematodes, insects and representatives of the order Acarina (acaricides). A drawback of such compounds, however, is that they possess a rather low persistence on the ground so that their insecticidal activity disappears after only a few days in the field.

Other compounds of the same class as above are disclosed in German Pat. No. 1,145,162 (known under the trade designation Aminocarb) and in U.S. Pat. No. 3,084,097 (known under the trade designation Zectran).

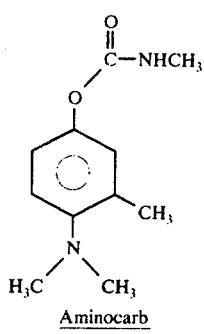

Aminocarb

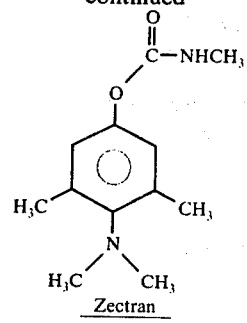

Zectran

These are proposed for combatting Coleoptera, Lepidoptera and Acari. Unfortunately, Aminocarb, Zectran and related compounds are also rather toxic to mammalians, having LD50 doses of 30 mg/kg and 15 mg/kg, respectively, when administered orally to test rats.

Thus, it is an object of the present invention to provide a new class of carbamates which exert an insecticide action while exhibiting a longer persistence in the field.

It is another object of this invention to provide a new class of carbamates which has a lower toxicity to warm-blooded animals than the carbamate insecticides of the prior art.

It is a further object of this invention to provide an improved method of combatting noxious insects through the use of the novel carbamates of this invention as insecticides in the field.

These and other objects which will be apparent from the following description are achieved by the present invention.

DESCRIPTION OF THE INVENTION

The compounds of this invention are N-(polychloroallyl)-amino phenols having the general formula:

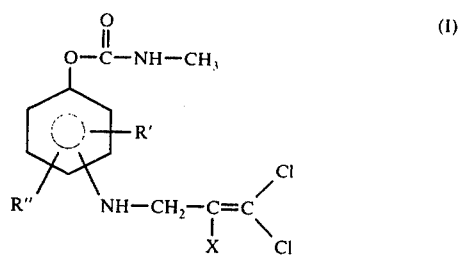

where X is selected from the group consisting of H, Cl and S-R''' where R''' is selected from the group consisting of lower alkyl, phenyl and substituted phenyl; R' and R'' are the same or different and are selected from the group consisting of H and $C_1$-$C_4$ alkyls.

The compounds of Formula I are prepared, in general, by reacting a substituted nitrophenol with methyl isocyanate, reducing the nitro substituent to amino and reacting the amino with a polychloroallyl halide in the presence of a base and halogenhydric end acceptor. Alternatively, the amino can be reacted with 3,3,3-trichloro-2X-propene, having the formula:

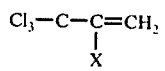

where X is as described in Formula I, above. The latter reaction, when catalyzed with potassium iodide, results in a purer product, which is a further object of the present invention.

Some of the more preferred carbamates of this invention are those having the following chemical formulae:

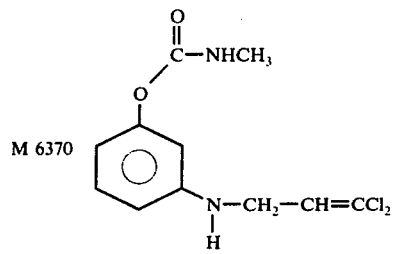

M 6370

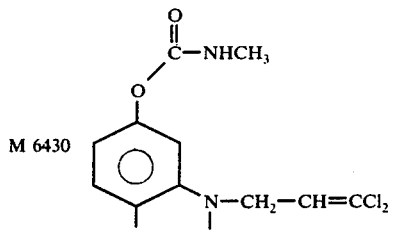

M 6430

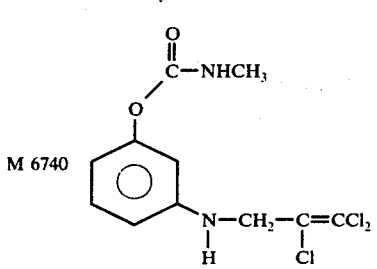

M 6740

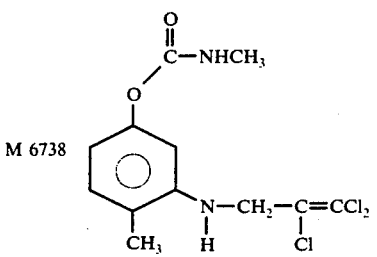

M 6738

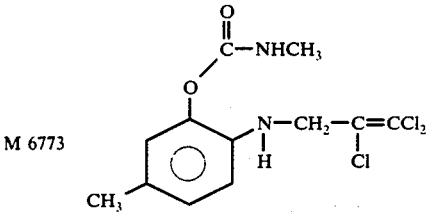

M 6773

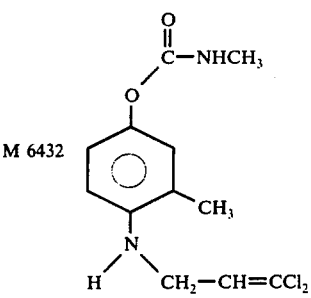

M 6432

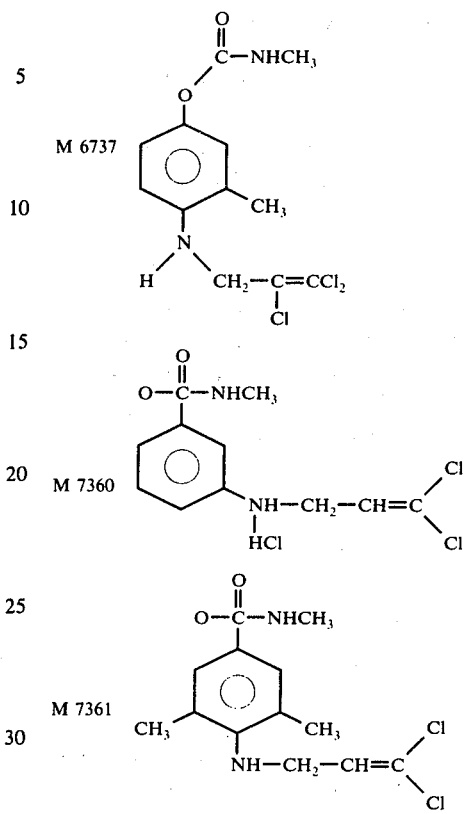

M 6737

M 7360

M 7361

These and other compounds prepared in the course of the research that has led to the present invention, have been identified through elemental analysis and infrared and nuclear magnetic resonance spectra.

The compounds of Formula I possess a high toxicity towards the parasites belonging to the following groups: Aphides, Diptera, Coleoptera, Lepidoptera, Acari and Nematoda, as resulting from the biological activity examples corresponding to the relevant tests. These compounds can be applied either to plants or in the environment to be disinfested, or directly to the insect to be killed, its habitat or its food.

The carbamate of active N-(polychloroallyl)-aminophenol may be given either by spreading it in the form of a powder or supported on or admixed with an inert carrier. It can also be sprayed as a solution or suspension in water or in other suitable solvents.

The compounds of this invention are relatively non-toxic to warm-blooded animals — their acute toxicity in rats, when given orally, often exceeds 100 mg/kg, as can be seen from Table 1 in which comparison is made between compounds according to this invention, identified by number, and known insecticides.

TABLE 1

| Acute Toxicity on White Rats, Administered Orally | |
|---|---|
| Compound | LD 50 (mg/kg) |
| Aminocarb | 30 |
| Zectran | 15 |
| M 6370 | 100 |
| M 6430 | 100 |
| M 6738 | 100 |

The persistence of the insecticidal activity of compounds according to this invention against various species has been studied in field tests, specifically by comparing the activity of the following compounds.

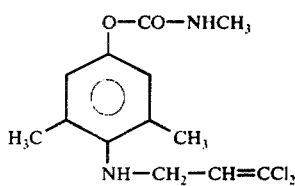

(our mark 7361)

N methyl carbamate of 3,5-methyl-4-(3,3-dichloro-allylamino-)-phenol

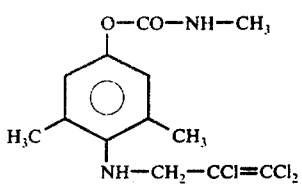

(our mark 8157)

N methyl carbamate of 3,5-methyl-4-(3,3 2 trichloroallylamino) phenol with the following compounds described in U.S. Pat. No. 3,819,678:

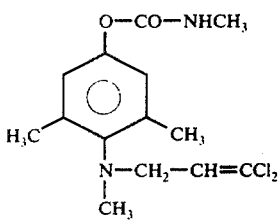

(hereinafter called M 7481)

N methyl carbamate of 3,5-methyl-4-(N-methyl, N,3,3-dichloroallyl-amino)-phenol

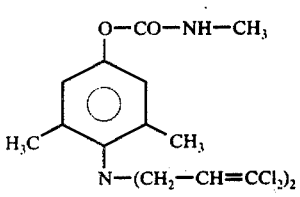

(hereinafter called M 7488)

N methyl carbamate of 3,5 methyl-4-(N-di-3, 3-dichloroallyamino)-phenol

As is shown in Tables 15, 16 and 17 and Examples 25, 26 and 27, following, the compounds of the invention possess a far longer persistence in the field than those of U.S. Pat. No. 3,819,678. This is most unexpected because in laboratory tests comparing the two respective class of these compounds, there is virtually no difference in insecticidal activity between them. For example, the N methyl-carbamate of N'-monosubstituted aminophenol of formula:

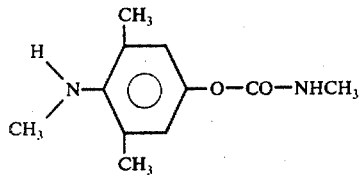

is only a bit less active than the N-dimethyl substituted homolog. (cfr. R. P. Miskus et al: Journal of Agricultural and Food Chemistry, Vol. 16, No. 4, pg. 605-607 - 1968). Yet, the compounds of these respective classes behave very differently in the field.

DESCRIPTION OF THE SPECIFIC EMBODIMENTS

The compounds, methods of preparation and methods of use are further illustrated in the following examples, which are not to be construed as limiting.

EXAMPLE 1

This example illustrates the preparation of N-methylcarbamate of 4-methyl-3-(3,3-dichloroallylamino)-phenol (M-6430).

A solution made up of 15.1 g of N-methylcarbamate of 4-methyl-3-amino-phenol and of 10.2 g of 3,3,3-trichloropropene in 50 ml of N,N-dimethylformamide was heated to 50° C., under stirring, for 8 hours, in the presence of 0.2 g of potassium iodide. After this time-period the reaction mass was cooled down to 20° C. and, at such temperature, 71. g of triethylamine were gradually added. The mixture was stirred for 30 minutes, then 100 ml of water and 80 ml of benzene were added, the two phases were separated and the aqueous phase was extracted again with 80 ml of benzene.

The benzene extracts, gathered together, were washed with water, then treated with a 1% HCl solution until reaching a pH = 4 and finally washed again with water.

The resulting organic phase was anhydrified on $Na_2SO_4$, the solvent was evaporated at 50° C. and 15 Torr, until an oily residue, weighing 6.5 grams, was obtained.

This residue, when subjected to chromatographic analysis on a thin layer, revealed a main component and three other components in smaller amounts.

The crude oil, left as is, solidified to yield a powder having a melting point of 80°–82° C. (sintering at 78° C.) which, after having been crystallized by a benzene/n-hexane mixture in a 1/1 ratio, yielded 5 grams of crystals having a melting point of 82°–83° C.

Analysis of $C_{12}H_{14}Cl_2N_2O_2$ $C_{calc}$: 49.85%; $C_{found}$: 49.69%. $H_{calc}$: 4.88%; $H_{found}$: 4.86%. $N_{calc}$: 9.69%; $N_{found}$: 9.35%.

EXAMPLES 2–6

Using the procedure described in Example 1, the compounds shown in Table 2 were prepared from the N-methylcarbamate of the corresponding amino-phenol.

TABLE 2

| Formula | Reference Number | M.P. ° C | Analysis Calc.% | Analysis Found% |
|---|---|---|---|---|
| OCONHCH₃ (structure) | M 6730 | oil | C 48.02<br>H 4.40<br>N 10.18<br>NMR consistent with the formula | C 46.03<br>H 4.05<br>N 9.22[a] |

TABLE 2-continued

| Formula | Reference Number | M.P. ° C | Analysis Calc.% | Found% |
|---|---|---|---|---|
| OCONHCH₃ (phenyl-NH-CCl=CHCCl) | M 6436 | 64–66° C | C 48.02<br>H 4.40<br>N 10.18<br>NMR consistent | C 46.91<br>H 4.26<br>N 9.26[a] |
| OCONHCH₃ (with CH₃ substituent) | M 6430 | 82–83° C | C 49.85<br>H 4.88<br>N 9.69 | C 49.69<br>H 4.86<br>N 9.35 |
| OCONHCH₃ (with CH₃ substituent, different position) | M 6432 | 107–109° C | $N_{tot.}$ 9.69<br>$N_{carb.}$ 4.85<br>Cl 24.53 | $N_{tot.}$ 9.41<br>$N_{carb.}$ 4.75<br>Cl 24.08 |
| OCONHCH₃ (with CH₃ substituent, ortho) | M 6529 | oil | C 49.85<br>H 4.88<br>N 9.69 | C 51.89<br>H 4.86<br>N 9.10[b] |

[a]From an analytical examination (chromatographic separation on a thin layer, NMR and elemental analysis) the product was found to contain impurities due to nitrogen dialkylated derivative.
[b]The compound was purified on a chromatographic column.

EXAMPLE 7

This example illustrates the preparation of N-methylcarbamate of 3-methyl-6-(2,3,3-trichloroallylamino)-phenol (M 6773).

A solution consisting of 15.1 g of N-methylcarbamate of 3-methyl-6-amino-phenyl and of 12.6 g of 1,2,3,3-tetrachloropropene in 30 ml of N,N-dimethylformamide was heated to 50° C. for 8 hours, under stirring, in the presence of 0.2 g of potassium iodide.

At the end of this time-period, the reaction mass was cooled to 20° C. and, at this temperature, 7.1 g of triethylamine were gradually added, always under stirring. The mixture was kept 2 hours under these conditions, then it was added with 100 ml of water and 100 ml of ethyl acetate and transferred into a separatory funnel. The two phases were separated and the aqueous phase was extracted again with 100 ml of ethyl acetate. The organic extracts, gathered together, were washed with water, then treated with a 1% HCl solution to a pH value of 5 and finally washed once more with water.

The resulting solution was anhydrified on $Na_2SO_4$, treated with decolorizing charcoal and filtered, and the solvent was evaporated at 40° C. and 15 Torr, until an oily residue, weighing 12.5 grams, was obtained. This residue, subjected to chromatographic analysis on a thin layer, revealed a main component and various impurities, two of which at not negligible concentrations. The crude oil solidified upon standing to a waxy solid which, after crystallization with 80 ml of 70% aqueous ethanol, yielded 8.1 g of crystals having a melting point of 127°–29° C.

Analysis of $C_{12}H_{13}Cl_3N_2O_2$: $C_{calc}$: 44.54% $C_{found}$: 44.66%. $H_{calc}$: 4.05%; $H_{found}$: 4.11%. $N_{calc}$: 8.65%; $N_{found}$: 8.51%. $Cl_{calc}$: 32.87%; $Cl_{found}$: 32.71%.

EXAMPLES 8–13

Using the procedure of Example 7, the compounds shown in Table 3 were prepared from the N-methylcarbamate of the corresponding aminophenyl.

TABLE 3

| FORMULA | Reference Number | M.P.=° C. | Analysis Calc% | Found% |
|---|---|---|---|---|
| OCONHCH₃ (phenyl-NH-CCl=CHCCl) | M 6740 | 106–108° C. | C 42.67;<br>H 3.58;<br>N 9.05; | 43.35<br>3.72<br>8.99 |

TABLE 3-continued

| FORMULA | Reference Number | M.P.=° C. | Analysis Calc% | Found% |
|---|---|---|---|---|
| 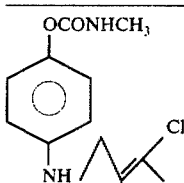 | M 6739 | 160-62° C. | C 42.67; H 3.58; N 9.05; | 42.74 3.63 9.11 |
| 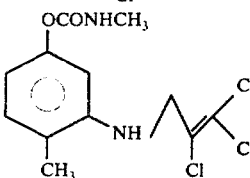 | M 6738 | 86° C. decomposition | C 44.53; H 4.04; N 8.65; | 44.80 4.35 7.90 |
| 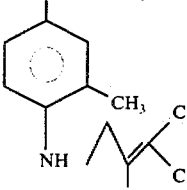 | M 6737 | 108-10° C. | C 44.53; H 4.04; N 8.65; | 45.87 4.43 8.55 |
| 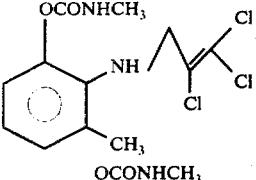 | M 6741 | 115-17° C. | C 44.54; H 4.05; N 8.65; | 45.28 4.19 8.77 |
| 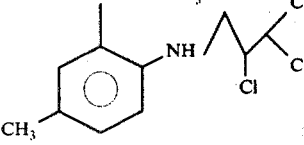 | M 6773 | 127-29° C. | C 44.54; H 4.05; N 8.65; Cl 32.87; | 44.66 4.11 8.51 32.71 |

EXAMPLE 14

This example illustrates the preparation of N-methylcarbamate of 3-(3,3-dichloro-2-phenylthio-allylamine)-phenol (M 6928).

A solution consisting of 8 g of N-methyl-carbamate of 3-amino-phenyl and of 10.5 g of 2-phenyl-thio-1,1,3-trichloropropene in 50 ml of N,N-dimethylformamide was kept at 50° C., under stirring, for 8 hours in the presence of 0.1 g of potassium iodide.

The reaction mass was cooled down to 20° C., then 4.1 g of triethylamine were added gradually and the mixture was kept at room temperature, always under stirring, for two hours. The mixture was then stirred with 50 ml of water and 50 ml of ethyl acetate, the whole was transferred into a separatory funnel and the aqueous phase was extraced two times with 100 ml of ethyl acetate.

The gathered organic extracts were washed with water, then treated with a 2% HCl solution until reaching a pH = 5, successively with a 4% NaHCO₃ solution and, finally, again with water. The resulting organic solution was anhydrified on Na₂SO₄ and evaporated at 50° C. and 15 Torr until obtaining 12.8 grams of an oily residue which, when subjected to chromatographic analysis on a thin layer, revealed a component having characteristics corresponding to those of the product to be obtained, as well as several other components, of which not all were at negligible concentrations.

The crude oil was dissolved in 150 ml of benzene and treated with decolorizing charcoal under intense stirring, at room temperature. The solution obtained by filtration from the charcoal was evaporated to a residual volume of 40 ml and added with 120 ml of n-hexane. A solid separated which, after filtering and air-drying, weighed 2.6 g and had a melting point of 60°-62° C.

Analysis of $C_{17}H_{16}Cl_2N_2O_2S$: $C_{calc}$: 53.27%; $C_{found}$: 52.9%. $H_{calc}$: 4.21%; $H_{found}$: 4.14%. $Cl_{calc}$: 18.50%; $Cl_{found}$: 18.04%. $N_{calc}$: 7.31%; $N_{found}$: 6.79%. $S_{calc}$: 8.37%; $S_{found}$: 8.87%.

EXAMPLES 15-16

Using the foregoing procedures, the compounds listed in Table 5 were prepared.

TABLE 5

| Formula | Reference Number | M.P., °C | Analysis Calc.% | Found% |
|---|---|---|---|---|
| [structure: OCONHCH₃ phenyl-NH-CH=CCl₂ · HCl] | M 7360 | 172° C. decomposition | Cl⁻ 11.38<br>Cl$_{tot.}$ 34.14 | 11.21<br>34.40 |
| [structure: OCONHCH₃ dimethylphenyl-NH-CH=CCl₂] | M 7361 | 96–98° C. | C 51.50<br>H 5.37<br>N 9.24<br>Cl 23.39 | 52.09<br>5.54<br>9.25<br>22.26 |

EXAMPLE 17

Biological Activity on Macrosiphum Euphorbiae (Aphides)

Potato seedlings, cultivated in pots, were infested with adult aphide females and, after a few hours, were sprayed with an aqueous dispersion of the compounds listed in Table 6. The mortality percentage was determined 24 hours after the treatment (on control non-treated seedlings, the mortality percentage was 0).

TABLE 6

Percentage of *Macrosiphum Euphorbiae* Females Dead After Treatment of Potato Seedlings With 0.01 Percent Dispersion of Compound

| Compound | Mortality Percent |
|---|---|
| Aminocarb* | 46 |
| M 6370 | 100 |
| M 6430 | 84 |
| M 6773 | 75 |

*comparison

EXAMPLE 18

Biological Activity on Culex Pipiens (Diptera)

Mosquito larvae of the third and fourth ages were introduced into glass pots containing an aqueous dispersion of the compounds shown at 2 ppm and 0.2 ppm. The percent mortality (glass pots containing pure water = 0) of the larvae 24 hours after the treatment is reported in Table 7.

TABLE 7

Percent Mortality of Mosquito Larvae in Glass Pots Containing 2 Parts per Million and 0.2 Parts Per Million, Respectively, of Active Principle, Aqueous Dispersion

| Compound | Percent of Mortality at Concentrations of | |
|---|---|---|
| | 2 ppm | 0.2 ppm |
| Aminocarb* | 25 | 0 |
| M 6370 | 94 | 17 |
| M 6430 | 100 | 80 |
| M 6740 | 100 | n.d. |
| M 6738 | 100 | n.d. | n.d. - not determined
*comparison

EXAMPLE 19

Biological Activity on Musca Domestica (Diptera)

Four day old adults were treated by topical application through a microsyringe with 1 mm³ of an acetonic solution of the compounds shown in such concentrations that they received doses of 5γ/insect; 2γ/insect; 0.5γ/insect of active principle. The mortality percentage 24 hours after the treatment is reported in Table 8 (mortality of insects treated with 1 mm³ of acetone = 0).

TABLE 8

Mortality Percentage of Adult Mosquitoes Treated with 5 γ, 2 γ and 0.5 γ of Active Principle Per Insect

| Compound | Percent of Mortality at Concentrations (per insect) of | | |
|---|---|---|---|
| | 5 γ | 2 γ | 0.5 γ |
| Aminocarb* | 85 | 50 | 0 |
| Zectran | n.d. | 60 | 0 |
| M 6430 | 100 | 100 | 100 |
| M 6738 | 100 | 100 | n.d. | n.d. - not determined
*comparison

EXAMPLE 20

Biological Activity on Leptinotarsa Decimlineata Coleoptera

Potato seedlings cultivated in pots were infested with 4-day old larvae and sprayed with an aqueous dispersion of the compounds according to this invention and Aminocarb as a comparison at doses of 0.1 and 0.11%; respectively. The mortality percentage is reported in Table 9. The mortality percentage of the control, untreated seedlings, was zero.

TABLE 9

Mortality Percentage of *Leptino Decemlineata* Larvae After Treatment with Aqueous Dispersions at 0.1 and 0.01 Percent of Active Principle

| Compound | Percent of Mortality Due to Treatment of the Seedlings With Dispersions of a.p. at | |
|---|---|---|
| | 0.1% concentr. | 0.01% concentr. |
| Aminocarb* | 100 | 45 |
| M 6370 | 100 | 100 |
| M 6430 | 100 | 100 |
| M 6740 | 100 | 100 |

TABLE 9-continued
Mortality Percentage of *Leptino Decemlineata* Larvae After Treatment with Aqueous Dispersions at 0.1 and 0.01 Percent of Active Principle

| Compound | Percent of Mortality Due to Treatment of the Seedlings With Dispersions of a.p. at | |
|---|---|---|
| | 0.1% concentr. | 0.01% concentr. |
| M 6738 | 100 | 100 |

*comparison

EXAMPLE 21

Biological Activity on Pieris Brassicae (Lepidoptera)

Cut leaves of cauliflower were sprayed with an aqueous dispersion of compound according to this invention at a 0.1% concentration. After drying, they were infested with 5-day old larvae. The mortality percentage is reported in Table 10. The mortality percentage of the control, untreated leaves, was zero.

TABLE 10
Percentage of Dead Larvae on Cauliflower Leaves Pretreated with an Aqueous Dispersion of Active Principle At 0.1 Percent

| Compound | Percent of Mortality |
|---|---|
| M 6370 | 90 |
| M 6430 | 100 |
| M 6432 | 100 |
| M 6737 | 100 |

EXAMPLE 22

Biological Activity on Tetranychus Urticae (Acari)

Small discs of bean leaves were infested with acarus eggs and successively treated by spraying with an aqueous dispersion of a compound of this invention and Aminocarb as a comparison, at concentrations of 0.1 and 0.01%. The percentage of mortality is reported in Table 11. The mortality percentage of the control, untreated discs, was zero.

TABLE 11
Mortality Percentage of Acari Eggs in Small Discs of Bean Leaves Treated with Aqueous Dispersion of Active Principle at 0.1 and 0.01 Percent Concentrations

| Compound | Percent of Mortality at Concentrations of | |
|---|---|---|
| | 0.1% | 0.01% |
| Aminocarb* | 40 | 0 |
| M 6737 | 100 | 80 |

*comparison

EXAMPLE 23

Biological Activity on Spodoptera Littoralis (Lepidoptera)

Cut tobacco leaves were sprayed with a 0.1% aqueous dispersion of compounds according to the present invention, shown in Table 12. After drying, the leaves were infested with 5-day old lepidopter larvae. The mortality percentages of the larvae 48 hours after the treatment are reported in Table 12. The mortality percentage of the control was zero.

TABLE 12
Mortality Percentage of *Lepidoptera* Larvae Forty-Eighy Hours After Treatment with Dispersion at 0.1 Percent of Active Principle

| Compound | Percent of Mortality |
|---|---|
| M 6432 | 100 |
| M 6737 | 100 |

EXAMPLE 24

Biological Activity on Meloidogyne Incognita (Nematoda)

A 1:1 mixture of field earth and sand infested by new-born larvae and eggs of the nematode was treated by uniformly mixing with a hydroacetone dispersion (20% by vol. of acetone) at a concentration of 0.1% and of 0.02% of the compounds under test so as to get soil samples containing 100 ppm and 20 ppm, respectively, of active principle. The soil was introduced into plastic pots and after 5 days, 5 tomato seedlings about 15 cm high were transplanted into each of them. Fourteen days after transplantation, the roots of the seedlings extracted from the soil were examined in order to determine the degree of infestation by counting the galls which had formed.

The nematocide activity is expressed in Table 13 as the percentage of infestation reduction with respect to the control (seedlings transplanted into the same soil treated with a dispersion free from active principle).

TABLE 13
Reduction Percentage of Nematode Infestation On Tomato Seedlings Grown in Soil Containing One Hundred Parts Per Million and Twenty Parts Per Million, Respectively, of Active Principle

| Compound | Reduction of Infestation | |
|---|---|---|
| | 100 ppm | 20 ppm |
| Aminocarb* | 95 | 0 |
| M 6370 | 100 | 100 |
| M 6430 | 100 | 88 |

*comparison

EXAMPLE 25

To show the variation in activity from one compound to another, depending on the species used, the activities of compounds according to this invention were investigated at different concentrations, expressed as percent of active principle, on various infesting species. The results are reported in Table 14. The mortality percentage was computed in the same way as in the preceding examples.

TABLE 14

Percentage of mortality on various infesting insects caused by compounds of this invention, at different active principle concentrations (in %)

| Reference Number | Structural Formula | Anti-cholesterase Activity | Macrosiphum % a.p. | Euphorbiae % mort. | Pieris % a.p. | Brassicae % mort. | Leptinot % a.p. | Decemlin % mort. | Culex p.p.m. a.p. | Pipiens % mort. | Tettran % a.p. | Urt. adults % mort. | Tettran % a.p. | Urt. eggs % mort. | Spodopt. % a.p. | Littoralis % mort. |
|---|---|---|---|---|---|---|---|---|---|---|---|---|---|---|---|---|
| M 7360 | O—CO—NH—CH$_3$ (phenyl) NH—CH$_2$—CH=CCl$_2$ | —HCl | 1<br>0,1<br>0,01 | 100<br>95<br>42 | 1 | 45 | 1<br>0,1<br>0,01 | 100<br>100<br>0 | 2<br>0,2<br>0,02 | 100<br>37<br>0 | 1 | 23 | 1 | 6 | | |
| M 7361 | O—CO—NH—CH$_3$ (2,6-dimethylphenyl with H$_3$C and CH$_3$) NH—CH$_2$—CH=CCl$_2$ | | 1<br>0,1<br>0,01 | 100<br>81<br>17 | 1<br>0,1<br>0,01 | 100<br>97<br>15 | 1<br>0,1<br>0,01 | 100<br>97<br>52 | 2 | 40 | 1<br>0,1 | 85<br>27 | 1 | 13 | 1<br>0,1<br>0,01 | 100<br>72<br>7 |

The following Examples, numbered 25-27, and the accompanying Tables are presented by way of comparing the persistence of insecticidal activity in the field between compounds according to this invention and compounds according to U.S. Pat. No. 3,819,678, referred to above.

EXAMPLE 25

The persistence of insecticidal activity in the field using the insect *Pieris brassicae* was examined as follows:

Cauliflower plants grown under natural conditions in the field were sprinkled with an aqueous suspension of compounds according to this invention identified hereinabove as M 7361 and M 8157. For purposes of comparison, cauliflower plants were sprinkled with an aqueous suspension of a compound according to U.S. Pat. No. 3,819,678, identified hereinabove as M 7481.

After the respective time periods shown in Table 15, leaves of the sprinkled plants were picked and brought to the laboratory where they were infested with 10-day old larvae of Pieris brassicae and then kept under observation. The percent of mortality of the insects was determined 48 hours after infestation in all cases. The results are summarized in Table 15. The percent mortality of the control, unsprinkled cauliflower leaves, was zero.

TABLE 15

Mortality Percent of *Pieris Brassicae* Larvae at Doses of 0.5 Percent of Insecticide

|  | 2 hours | 5 days | 9 days | 14 days | 17 days | 22 days |
|---|---|---|---|---|---|---|
| M 7361 | 100 | 100 | 100 | 100 | 100 | 100 |
| M 8157 | 100 | 100 | 100 | 100 | 100 | 100 |
| M 7481* | 100 | 55 | 30 | 0 | 0 | 0 |

*comparison

It is shown that the insecticides of this invention, M 7361 and M 8157, fully retain their insecticidal activity in the field for periods of at least 22 days after application, while the prior art insecticide, M 7481, begins to lose its activity within 2 to 5 days and is totally ineffective after only 14 days.

EXAMPLE 26

The persistence of insecticidal activity in the field using the insect *Spodoptera littoralis* was examined as follows:

Ricinus plants grown in the field under natural conditions were sprinkled with an aqueous suspension of the insecticidal compounds according to this invention designated hereinabove as M 7361 and M 8157. For purposes of comparison, an aqueous suspension of each of M 7481 and M 7488, according to U.S. Pat. No. 3,819,678 and identified above, was sprinkled on similarly grown Ricinus plants.

After the time periods shown in Table 16, leaves of the sprinkled plants were picked and brought to the laboratory where they were infested with 10-day old larvae of Spodoptera littoralis and then kept under observation. After 48 hours, the percent of mortality of the insects was determined, and the results are summarized in Table 16. The mortality percent of the control unsprinkled leaves was zero.

TABLE 16

Mortality Percent of *Spodoptera Littoralis* Larvae at Doses of One Percent of Insecticide

|  | 2 hours | 5 days | 11 days | 14 days | 18 days | 25 days |
|---|---|---|---|---|---|---|
| M 7361 | 100 | 100 | 100 | 100 | 100 | 100 |
| M 8157 | 100 | 100 | 100 | 100 | 100 | 100 |
| M 7481* | 100 | 100 | 77 | 60 | 47 | 40 |
| M 7488* | 100 | 92 | 47 | 38 | 22 | 0 |

*comparison

Here too, using a different species of insect for test purposes, the compounds of the present invention exhibit a much greater degree of persistence in insecticidal activity in comparison with those of U.S. Pat. No. 3,819,678 after application and exposure to natural, real-life conditions.

EXAMPLE 27

The persistence of insecticidal activity in the field using the insect Leptinotarsa decemlineata was examined as follows:

Potato plants grown in the field under natural conditions were sprinkled with an aqueous suspension of compound M 7361 which is according to this invention and identified hereinabove. For purposes of comparison, similarly grown potato plants were sprinkled with an aqueous suspension of the compounds M 7488 and M 7481, respectively, both according to U.S. Pat. No. 3,819,678 and identified above.

After the time periods shown in Table 17, leaves of the sprinkled plants were picked and brought to the laboratory where they were infested with 10 day-old larvae of Leptinotarsa decemlineata and then kept under observation. After 48 hours, the percent of mortality of the insects was determined. The results are shown in Table 17. The mortality percent of the control unsprinkled leaves was zero.

TABLE 17

Mortality Percent of *Leptinotarsa Decemlineata* at Doses of 0.2 Percent

|  | 2 hours | 4 days | 7 days | 11 days | 18 days | 25 days |
|---|---|---|---|---|---|---|
| M 7361 | 100 | 100 | 100 | 100 | 100 | 73 |
| M 7481* | 100 | 60 | 20 | 0 | 0 | 0 |
| M 7488* | 100 | 70 | 20 | 10 | 0 | 0 |

*comparison

From the above, it is demonstrated that the compounds according to this invention consistently display a longer persistence of insecticidal activity under field conditions in comparison with those of the prior art as represented by U.S. Pat. No. 3,819,678.

Other modifications and variations of the present invention are possible in the light of the above description. It is to be understood, therefore, that changes may be made in the particular embodiments disclosed above which are within the full intended scope of the invention as defined in the appended claims.

We claim:

1. An insecticidal agent, said agent being a compound having the general formula:

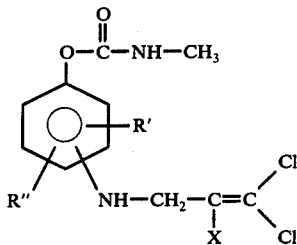

where X is selected from the group consisting of H, Cl and S-R''' where R''' is selected from the group consisting of lower alkyl and phenyl; and R' and R'' are the same or different and are selected from the group consisting of H and $C_1$-$C_4$ alkyls.

2. An insecticidal composition comprising, in admixture, an insecticidally effective amount of an insecticidal agent having the general formula:

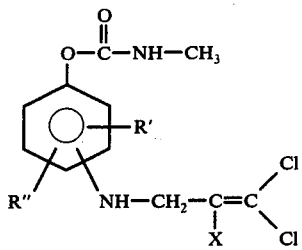

where X is selected from the group consisting of H, Cl and S-R''' where R''' is selected from the group consisting of lower alkyl and phenyl; and R' and R'' are the same or different and are selected from the group consisting of H and $C_1$-$C_4$ alkyls, and an inert carrier therefor.

3. An insecticidal composition comprising a solution or suspension in water or other suitable solvent of an insecticidally effective amount of an insecticidal agent having the general formula:

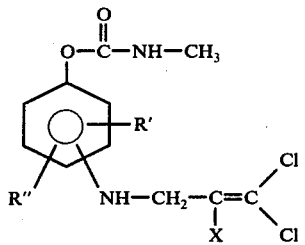

where X is selected from the group consisting of H, Cl and S-R''' where R''' is selected from the group consisting of lower alkyl and phenyl; and R' and R'' are the same or different and are selected from the group consisting of H and $C_1$-$C_4$ alkyls.

4. A composition as defined in claim 3 which comprises a solution or suspension of said insecticidal agent in water.

5. A composition as defined in claim 3 which comprises a solution of said insecticidal agent in acetone.

6. A method of combatting infestations by insects from among Diptera, Coleoptera, Lepidoptera, Aphides, Acari and Nematodes, the method comprising spraying said insect or insects or the habitat of said insect or insects or the food of said insect or insects with an insecticidal agent having the general formula:

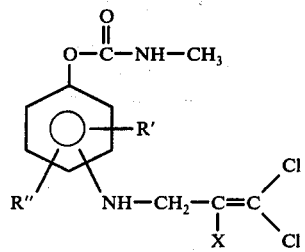

where X is selected from the group consisting of H, Cl and S-R''' where R''' is selected from the group consisting of lower alkyl, phenyl and substituted phenyl; and R' and R'' are the same or different and are selected from the group consisting of H and $C_1$-$C_4$ alkyls, as such, in admixture with an inert carrier or in the form of a solution or suspension, in concentrations of at least 0.1 percent of active principle.

7. A method of combatting insect infestations for longer periods of time in the field comprising spraying said insect or its food, habitat or environment with an insecticidally effective amount of an insecticidal agent having the general formula:

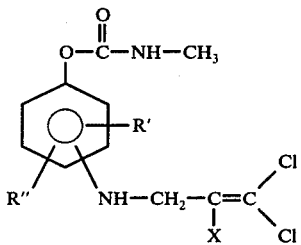

where X is selected from the group consisting of H, Cl and S-R''' where R''' is selected from the group consisting of lower alkyl and phenyl; and R' and R'' are the same or different and are selected from the group consisting of H and $C_1$-$C_4$ alkyls, said compound having a longer persistence in the field.

* * * * *